United States Patent [19]

Kim

[11] Patent Number: 5,682,219
[45] Date of Patent: Oct. 28, 1997

[54] EYESHADE SPECTACLES

[76] Inventor: Dong Soo Kim, 109-3, Dongsan-dong, Koyang-shi, Kyongki-do, Rep. of Korea

[21] Appl. No.: 591,296

[22] Filed: Jan. 25, 1996

[30] Foreign Application Priority Data

Jan. 25, 1995 [KR] Rep. of Korea ............... 95-1129
Jan. 9, 1996 [KR] Rep. of Korea ............... 96-153

[51] Int. Cl.$^6$ ............... G02C 7/10; G02C 1/00; A61F 9/00
[52] U.S. Cl. ............... 351/41; 351/44; 351/158; 2/12
[58] Field of Search ............... 351/41, 44, 45, 351/63, 158; 2/10, 12, 454

[56] References Cited

FOREIGN PATENT DOCUMENTS 1036013 9/1953 France ............... 2/12

*Primary Examiner*—Huy Mai
*Attorney, Agent, or Firm*—Birch, Stewart, Kolasch & Birch, LLP

[57] ABSTRACT

Eyeshade spectacles containing a light shield body, and the supporting materials to wear it, whereby the eyeshade spectacles assist the user in focusing his mind and dilating the pupils of the eye due to the difference in luminous intensity.

7 Claims, 4 Drawing Sheets

EYESHADE SPECTACLES

BACKGROUND AND SUMMARY OF THE INVENTION

1. Field of the Invention

The present invention relates to the eyeshade spectacles for the concentration of mind. More particularly, the present invention is concerned with eyeshade spectacles and eyeshade spectacles attached to a cap which helps the user concentrate with his mind on specific subjects, e.g. a computer, a television set, a book, and a field game, an the like. The eyeshade spectacles of the present invention can be used as a kind of telescope in which the lens of the eyeball functions as the eyeglass and the eyeshade helps to dilate the pupil for achieving improved eyesight without the aid of a lens.

2. Description of the Prior Arts

In our present society where the function of the eyes to observe is very important, the eyeshade spectacles were developed to facilitate reading and viewing at a glance specific objects in a room, such as a computer, a television set, fishing, outdoor athletic competition, books and so forth. Advantageously, the device of the present invention is made to be attached to the visor of a cap. Heretofore, the protection of the eyes and the correction of eye sight were the main fuctions of eye spectacles, neglecting or overlooking the effect and the necessity of eyeshade spectacles that provide shadows to the eyes.

Most spectacles are used for the protection and the improvement of eyesight. However, the present inventor has invented the eyeshade spectacles as shown in FIG. 2, so that the user can concentrate his mind by shading his eyes with the light shield. For a long time, human beings have shaded their eyes with their hand to achieve a more improved eyesight, especially in the daylight as shown in FIG. 1. The present inventor has applied the above principle to eyeshade spectacles. The eyeshade spectacles of the present invention externally resembles some specific spectacles like 3-D spectacles, but it differs from them because it has no lens or other eye cover. For the concentration of the mind, Korea Patent Pub. No. 89-2904 describes an eyeshade-attached cap. However, in this case of a mind concentration cap, a left shade and a right shade were attached to the visor of cap. By the present invention, the effect of mind concentration and protecting the eyes from shadow was improved by attaching the left and right shades attached to the visor of a cap, compared to the existing visor of a cap. However, in conventional eye shades the exposure to the ground was open. Reflection of light from the ground and water surface is most severe, but with that known device, the reflection of light from the surface of ground and water could not be shaded. Therefore, its effect was limited extremely.

The present inventor invented an eyeshade spectacles as shown in FIG. 2, which forms the shadow around the eye spectacles socket by the four-cornered light shield. The eyeshade aids the user in focusing his mind and also dilates the pupils due to the difference in the luminous intensity.

OBJECT OF THE INVENTION

The object of the present invention is to provide a novel eyeshade spectacles which can help the user to concentrate his mind on specific subjects, i.e., a computer, a television, a book, a field game, etc. by shading the eyes with a light shield.

The eyeshade spectacles of the present invention is composed of a four-cornered light shield, and a band or two templates attached to the light shield. In another embodiment, the eyeshade spectacles is composed of a light shield to attached to the visor of a cap.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE INVENTION

According to the present invention, no light-filter or light-transmission element, such as lenses or transmission film, is attached to the light shield body(tube) in front of the eyes. Instead, a jutted light shield body which creates shade is placed in front of the left and right eyes so as to form a darkened area of a certain length and width surrounding the eyes. The degree of light surrounding the object to be seen is much brighter than that in front of the eyes. The difference in brightness and darkness hightens the adjustability of the pupils and contributes to emotional stability, thereby maximizing the effect of mind concentration.

Figure 1:
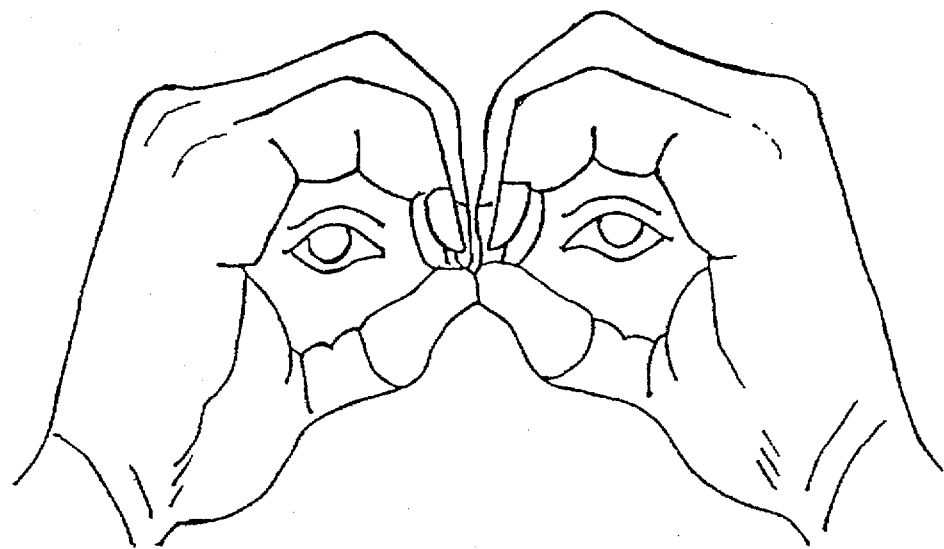
FIG. 1 illustrates the principle of the eyeshade spectacles, which shows how a person frequently shades his eyes with his hands.

People frequently form a shade effect around their eyes with their hands shaped as shown in FIG. 1, when it is desired to intensely observe an object. It is our experience that an object in a bright location can be better seen from a dark place like in a room or a car. For the present invention, this principle is utilized. A certain width of dark surroundings is provided in front of and around the eyes, so as to discern an object much better, with the dark functioning as the light passage. This is the nature of the present invention, and an effect incidental to it is the protection of the eyes.

Of the specific spectacles to observe water, snow or weather phenomena, a design similar to the present invention does exists. However, the differences between the present invention and the known devices are as follows: (1) the present invention has a completely open space in front of the eyes, and (2) the light shield body is made to produce shade in the form of a dark space in front of and around the eyes. The present invention is entirely different in view of the eye sight promotion effect incidental only to the eyeshade spectacles produced through the ideal combination of the above two effective functions. The deep meaning of nature seen seeing through open space is the best spectacles which are identified by the present invention. This is achieved by placing a light shield body of square type or oval type in front of the eyes. The present invention is also effective for the promotion of eye sight by shading all around the eyes to form a dark environment around the eyes. The structure of the present invention is simple, and is easy to produce it. Its form is variable in the form of spectacle frames. Its utility is also versatile in its attachment to the visor of a cap. By attaching the eyeshade spectacles according to the present invention to the visor of a cap, the same effect as that shown in FIG. 1, wherein the principle of the present invention is shown, is achieved easily.

FIG. 1 shows the principle of the eyeshade spectacles of the present invention. It shows a person shading his eyes with his hands. If the frame of the conventional spectacles extends front and rear, the body of the eyeshade spectacles will be formed.

Figure 2:
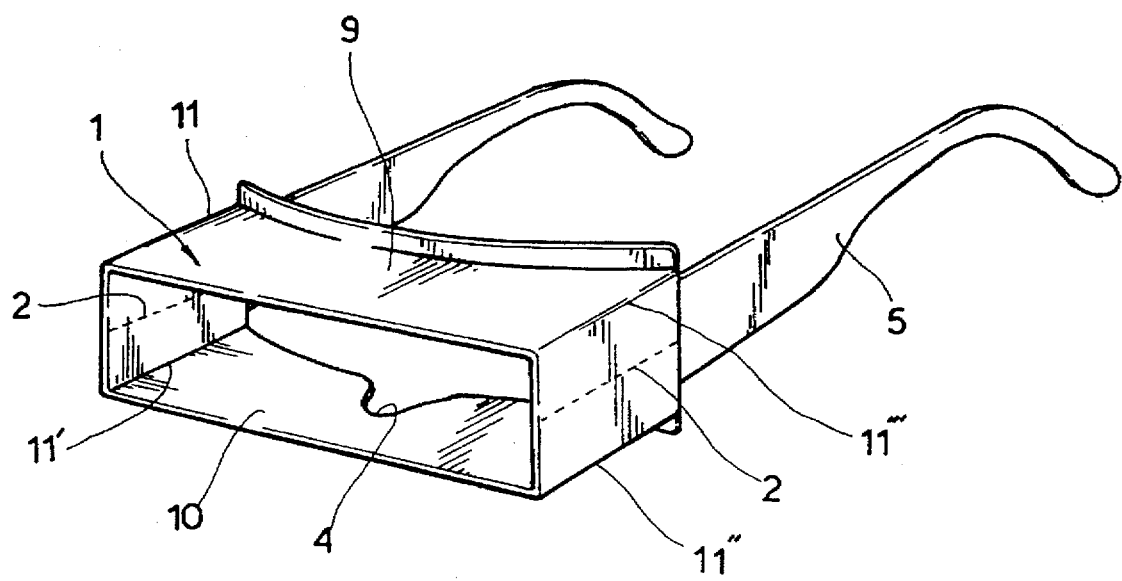
FIG. 2 is a perspective view of the eyeshade spectacle of the present invention.

FIG. 2 shows an example of the eyeshade spectacles of the present invention. The hexahedral light shield body (1) having open ends can be folded and unfolded along the edges (11, 11', 11", 11'"), or along the central lines of the lateral sides (2, 2'). It can be worn by the band or templates (5) which are attached to the lateral sides of the rear body of the eyeshade spectacles. The lower side of the eyeshade spectacles (10) can be grooved to place the eyeshade spectacles on the nose (4) and can be shorter than the upper side (9) for wearing comfort and for achieving a wide field of vision.

Figure 3:
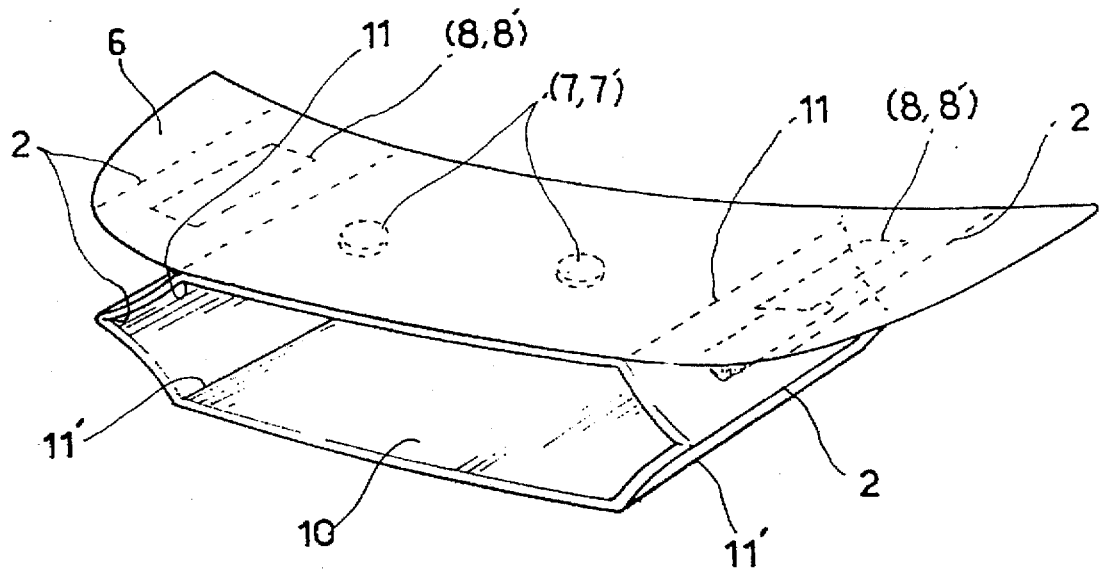
FIG. 3 illustrates the body of the eyeshade spectacles attached to the visor of a cap.

FIG. 3 shows the eyeshade spectacles attached to visor (6) of a cap. The band (5) of the eyeshade spectacles shown in FIG. 2 can be removed to connect the eyeshade spectacles with the visor (6) by snaps, magic tapes or magnets (7, 7') which are attached to the upper side of the eyeshade spectacles (9) and the lower side of the visor (6). In the case of FIG. 3, the eyeshade spectacles (1) of the present invention can be attached to or detached freely from the visor (6) of the cap.

Figure 4:
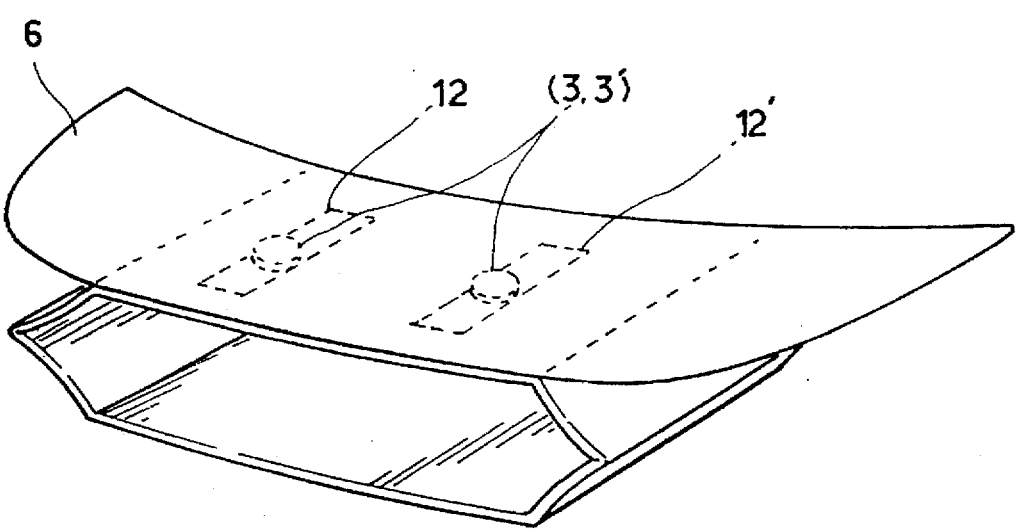
FIG. 4 illustrates another example of the eyeshade spectacles attached to the visor of a cap.

FIG. 4 shows another embodiment of the eyeshade spectacles attached to the visor (6) of the cap in which the upper side of the eyeshade spectacles (1) and the lower side of the visor (6) are attached by the guide (12, 120 and the guide bar (3, 3'), respectively. At this time, the eyeshade spectacles can be moved from front to rear along the guide (12, 12'). The eyeshade spectacles (1) can be folded or unfolded by attaching or detaching the lateral sides of it to the lower side of the visor (6) with the snaps, the magic tapes, or the magnets (8, 8').

Figure 5:
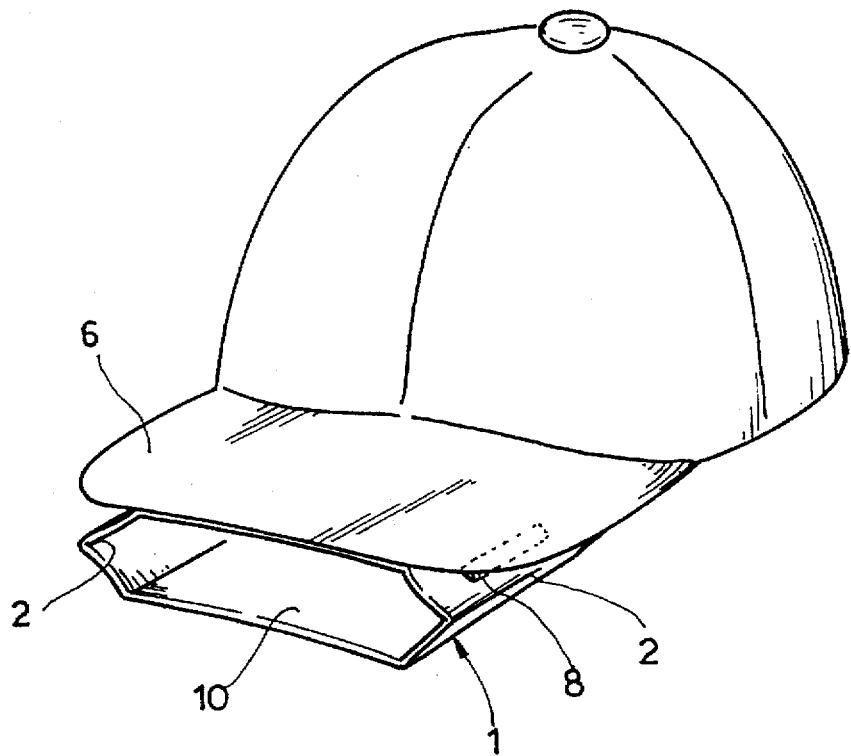
FIG. 5 is a view of the eyeshade spectacles attached to the cap.

FIG. 5 shows the eyeshade spectacles attached to visor (6) of a cap.

Figure 6:
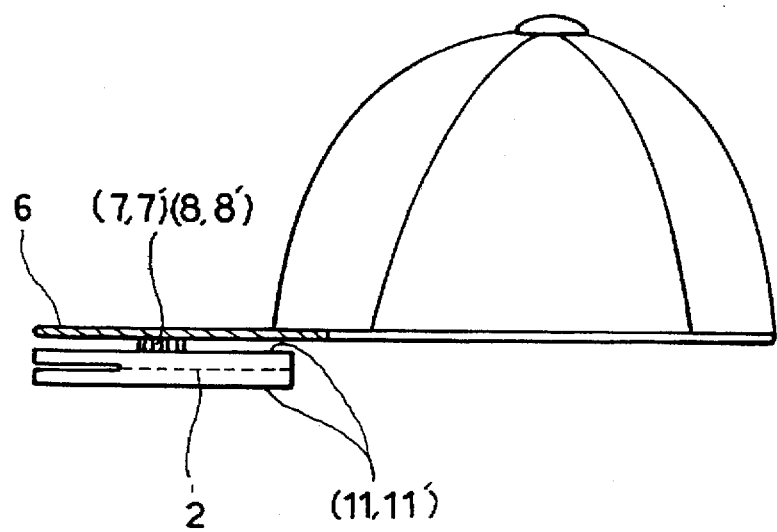
FIG. 6 is a side view of the eyeshade spectacles attached to the cap when the eyeshade is in a collapsed state.

FIG. 6 shows the side view of the eyeshade-attached visor (6) where the eyeshade spectacles are folded.

Figure 7:
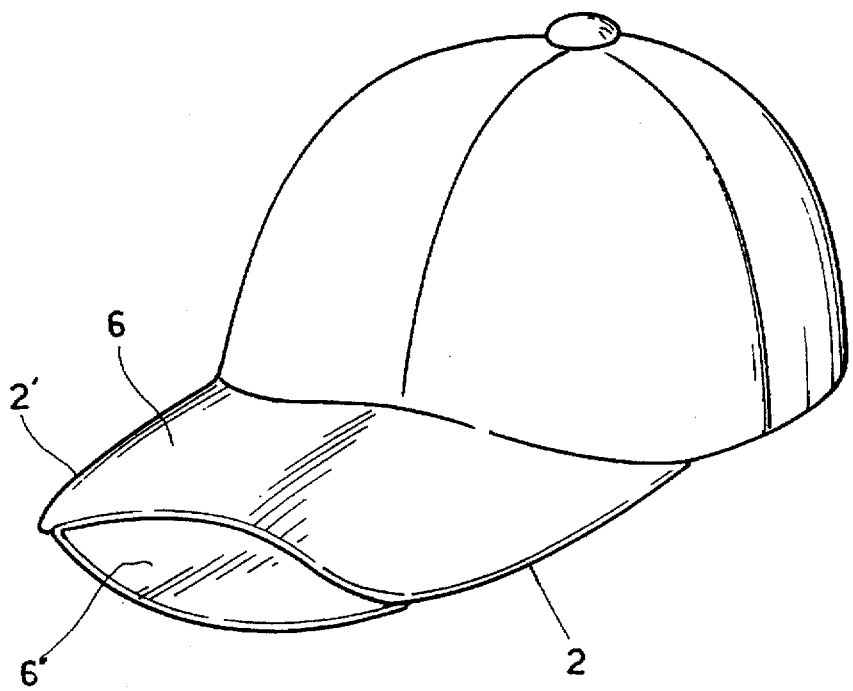
FIG. 7 is another example of the eyeshade spectacles in which the visor itself functions as an eye shield.

FIG. 7 shows another embodiment of the eyeshade spectacles in which the visor itself is the eyeshade spectacles (1). The visor (6) of the present invention is composed of two folds, i.e., the upper visor (6) and the lower visor (6'). The lower visor (6') can be widened for the use of the eyeshade spectacles. It can be folded by attaching the lower visor (6') to the upper visor (6) with snaps, magic tapes or magnets (7, 7') which are installed in the lateral sides of the inner visors.

Figure 8:
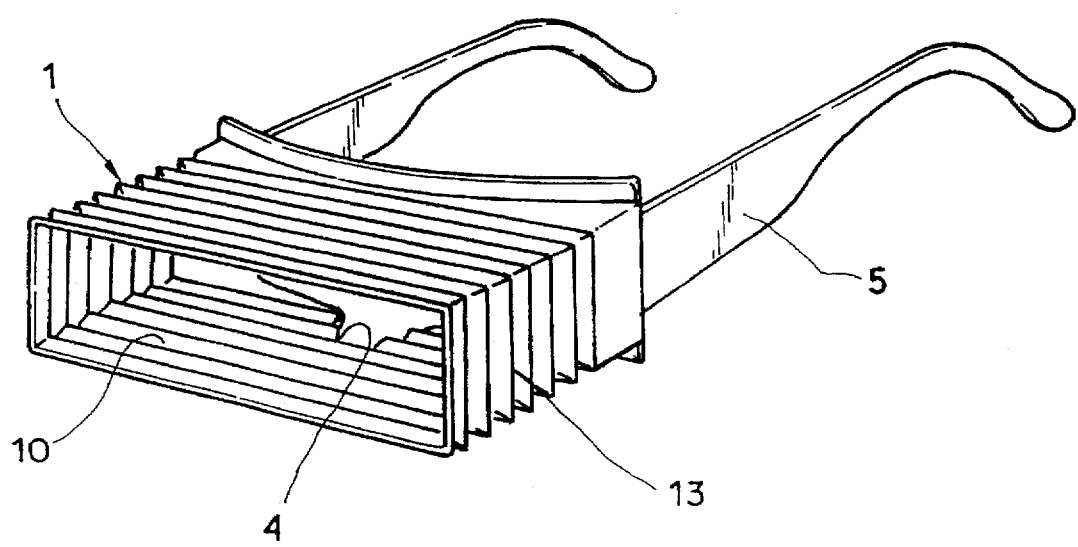
FIG. 8 is view of an eyeshade spectacles which has an accordion style configuration.

FIG. 8 shows another embodiment of the eyeshade spectacles (1) which has an accordion style body. The body of the eyeshade spectacles can be folded by many pleats (13), convenient for storage.

The eyeshade spectacles (1) of the present invention can be made of conventional paperboard, plastic, or cellulose substances. Preferably, the inner side of the eyeshade is made of light-absorbent material, or coated with a light-absorbing substance.

The thus produced invention has the same effect as a middle road effect between a microscope and a telescope. With eye balls as lenses, and with the dark surroundings provided by the light shield body to create shade compared to the outside brightness, the light collection ability of pupils which naturally adjusts to the brightness and darkness of nature, is hightened, so that a specific object can be seen directly without complementary lenses. As the light of a star is shaded by the light of the sun in daytime, eyes fail to catch the lesser light under the brighter light. However the darkness enlivens the light so as to make it shine. The eyeshade spectacles are made to enliven the object in lesser light, which otherwise might not be seen under a stronger light of the sun or artificial light, so that it could be readily received in the eyes.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. Eyeshade spectacles which comprise a light-shielding body having edges which define an enclosure with opposing open ends, said light-shielding body being foldable along its edges.

2. The eyeshade spectacles of claim 1, wherein template means are attached to said light-shielding body for securing the light-shielding body to the eyes of the user.

3. The eyeshade spectacles of claim 2, wherein the enclosure contains lateral sides having additional fold lines.

4. The eyeshade spectacles of claim 1, wherein the light-shielding body contains a multiplicity of pleats which define an accordion-style body which is foldable.

5. A cap containing a visor having a top side and an underside, and eyeshade spectacles removably attached to said underside of the visor, said eyeshade spectacles comprising a light-shielding body having edges which define an enclosure with opposing open ends, said light-shielding body being foldable along its edges.

6. The cap of claim 5, wherein the light-shielding body is attached to the visor by guides and guide bars which enables the light-shielding body to be moved along the visor between the front and rear of the cap.

7. A cap containing an upper and lower visor which when separated from each other form a light-shielding body with edges which define an enclosure with opposing open ends, said visors being collapsible on each other by attaching the upper visor to the lower visor.

\* \* \* \* \*